(12) United States Patent
Main et al.

(10) Patent No.: US 10,653,449 B2
(45) Date of Patent: May 19, 2020

(54) CANNULA SEALING

(71) Applicant: SURGICAL INNOVATIONS LIMITED, West Yorkshire (GB)

(72) Inventors: David Andrew Main, West Yorkshire (GB); Christopher David Harrison, West Yorkshire (GB)

(73) Assignee: SURGICAL INNOVATIONS LIMITED, Leeds, West Yorkshire (GB)

( * ) Notice: Subject to any disclaimer, the term of this patent is extended or adjusted under 35 U.S.C. 154(b) by 361 days.

(21) Appl. No.: 15/542,134

(22) PCT Filed: Jan. 11, 2016

(86) PCT No.: PCT/GB2016/050057
§ 371 (c)(1),
(2) Date: Jul. 7, 2017

(87) PCT Pub. No.: WO2016/110720
PCT Pub. Date: Jul. 14, 2016

(65) Prior Publication Data
US 2018/0021063 A1 Jan. 25, 2018

(30) Foreign Application Priority Data
Jan. 9, 2015 (GB) .................................. 1500328.8

(51) Int. Cl.
*A61B 17/34* (2006.01)
(52) U.S. Cl.
CPC .......... *A61B 17/3498* (2013.01); *A61B 17/34* (2013.01); *A61B 17/3474* (2013.01);
(Continued)

(58) Field of Classification Search
CPC ............ A61B 17/3498; A61B 17/3474; A61B 17/3462; A61B 17/34; A61B 2017/3464
See application file for complete search history.

(56) References Cited

U.S. PATENT DOCUMENTS 7,785,294 B2 8/2010 Hueil et al.
8,409,146 B2 4/2013 Judson et al.
(Continued)

FOREIGN PATENT DOCUMENTS

CN 1788690 A 6/2006
DE 202008009527 U1 10/2008
(Continued)

OTHER PUBLICATIONS

International Search Report and Written Opinion in corresponding International Patent Application No. PCT/GB2016/050057, dated Mar. 9, 2016. 11 pages.
(Continued)

*Primary Examiner* — Theodore J Stigell
(74) *Attorney, Agent, or Firm* — Leason Ellis LLP

(57) ABSTRACT

A surgical access device comprises a seal assembly (51) having a plurality of part circular sealing members (55) each attached to a common ring (53) which is held within the device about its longitudinal axis. In use, the sealing members are located radially inwards of the ring in a stacked relationship. When not within the device, the sealing members are movable from a position radially outwards of the ring to a position radially inwards of the ring. A seal core comprises the seal assembly and a protective member which, in use, is located on the proximal side of the seal assembly. A method of assembling the surgical access device is also provided.

14 Claims, 14 Drawing Sheets

(52) U.S. Cl.
CPC ... *A61B 17/3462* (2013.01); *A61B 2017/3419* (2013.01); *A61B 2017/3464* (2013.01)

(56) References Cited

U.S. PATENT DOCUMENTS

| | | | |
|---|---|---|---|
| 2008/0146882 A1* | 6/2008 | Cropper | A61B 17/3423 600/206 |
| 2014/0201966 A1 | 7/2014 | Campbell et al. | |

FOREIGN PATENT DOCUMENTS

| | | | |
|---|---|---|---|
| EP | 2138112 A1 | 12/2009 | |
| JP | 2001128985 A | 5/2001 | |
| WO | 2014044665 A1 | 3/2014 | |

OTHER PUBLICATIONS

International Preliminary Report on Patentability in corresponding International Patent Application No. PCT/GB2016/050057, dated Jul. 11, 2017. 7 pages.

\* cited by examiner

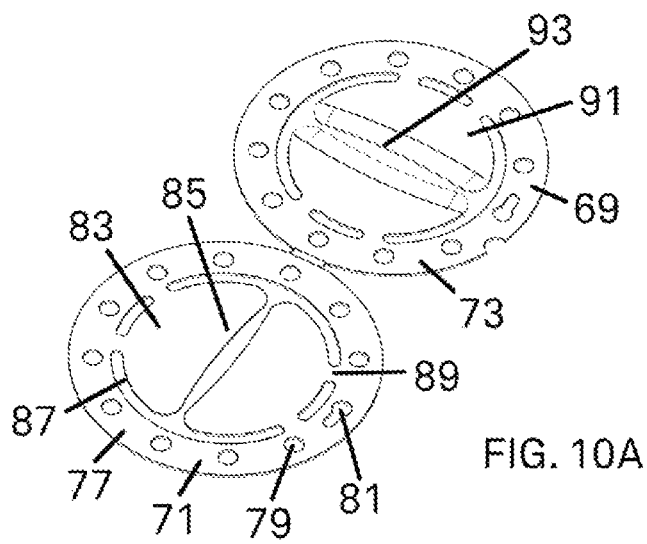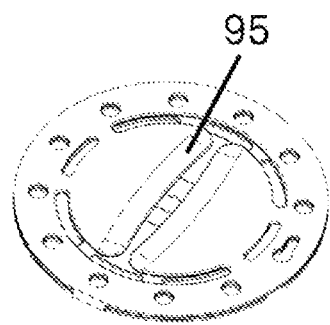
FIG. 10A  FIG. 10B
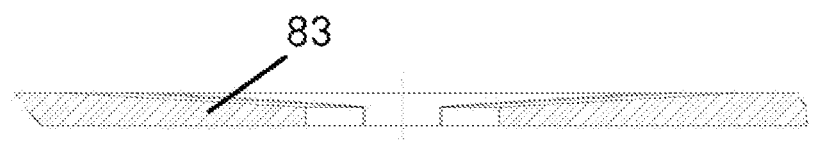
FIG. 11
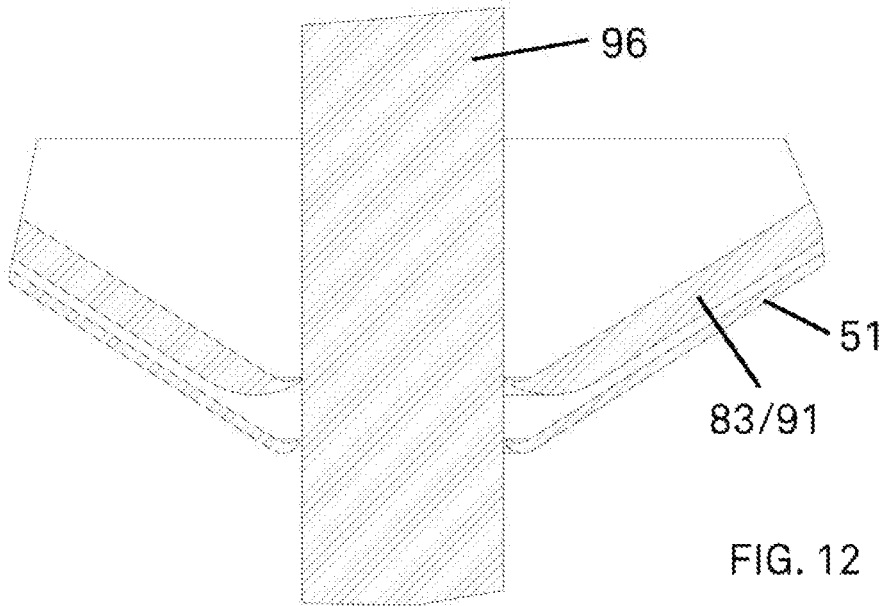
FIG. 12

CANNULA SEALING

CROSS-REFERENCE TO RELATED PATENT APPLICATIONS

This application is a U.S. National Phase Application under 35 U.S.C. § 371 of International Patent Application No. PCT/GB2016/050057, filed Jan. 11, 2016, and claims the priority of GB1500328.8, filed Jan. 9, 2015, all of which are incorporated by reference in their entireties. The International Application was published on Jul. 14, 2016 as International Publication No. WO 2016/110720 A1.

FIELD OF THE INVENTION

The invention relates to surgical access devices and particularly, though not exclusively, to such devices for use in laparoscopy.

BACKGROUND TO THE INVENTION

Laparoscopic ports facilitate access to the abdominal cavity during endoscopic or minimally invasive surgery. Laparoscopic entry devices require seals to prevent or minimise leakage of insufflation gas through the port when surgical instruments are inserted.

During minimally invasive abdominal surgery, the patient is insufflated with carbon dioxide in order to create space between internal organs and other bodily tissue and thereby create a usable workspace for the surgeon to undertake a given procedure. For this reason a critical feature of any laparoscopic port access system is to ensure that no insufflation gas leaks through the port when instruments of varying sizes are inserted.

During use, the port is first used to puncture the abdominal wall to create an access point through which the surgeon gains access to the abdominal cavity. This puncture is achieved via a component of the port assembly known as the trocar or obturator. The trocar or obturator is then subsequently removed from the assembly leaving the cannula in place, protruding through the abdominal wall of the patient. The patient can then be insufflated, with the cannula remaining in place, to provide the surgeon with an access point to the surgical site—the abdominal cavity. The cannula is the part of the port assembly which contains the seals.

The insufflation gas is prevented from leaking through the cannula due to the presence of a non-return valve within the device. There are several types of non-return valve that can be employed within a cannula body to facilitate this, including flap valves, duckbill valves and quad type valves.

When a surgical instrument is inserted through the port assembly, the non-return valve is forced open. A further seal assembly is therefore required, capable of conforming to the diameter of surgical instruments, to maintain insufflation pressure when the non-return valve is open.

When a surgical instrument is removed from the port assembly, the non-return valve automatically closes, thus preventing leakage of the insufflation gas through the port assembly.

The further seal assembly is a critical aspect a laparoscopic port system. The most basic seal employed to achieve the required functionality is a simple lip seal. This is typically a single piece elastomeric component, consisting of an outside diameter designed to fit inside the cannula housing, and an inside diameter designed to seal around the outside diameter of a surgical instrument. The disadvantage of this form of seal is that it is only designed to seal around one specific diameter of instrument. Therefore, if differing diameter instruments need to be used then more than one port needs to be inserted. To combat this problem, ports using simple lip seals need to incorporate several seals of different diameters which can be manually selected by the user.

One such way this has been achieved is described in GB2441113 which discloses a port system with 3 simple lip seals of different diameters which can be manually selected via pivots on the cannula body. Although a configuration such as this does allow the device to be used with instruments of different diameters, it is undesirable that the user has to manually switch between seals when using multiple instruments of different diameters.

To overcome this requirement for manual seal selection, efforts have been undertaken to develop an improved single or universal seal assembly, capable of automatically conforming to a range of different diameters.

The first universal seal for a port system was described in U.S. Pat. No. 5,395,342 which discloses a seal with a simple conical elastomeric component with a hole at the apex. This elastomeric cone is assembled over a plurality of resilient legs extending inwardly from the inside diameter of the cannula housing.

When an instrument is inserted through the cannula, the distal tip of the instrument firstly makes contact with the resilient legs. The resilient legs are then forced outwards, causing the hole in the apex of the elastomeric cone to dilate to the size of the instrument diameter.

A disadvantage of this solution is the force required to insert a large diameter instrument through the assembly. The user typically desires to feel as little resistance as possible when inserting an instrument through a cannula. This high resistance is due to the fact that a single elastomeric component is being required to expand from below 5 mm diameter to above 12 mm diameter.

Another disadvantage is the high level of friction between the instrument shaft diameter and the seal assembly.

To overcome these problems, seal assemblies comprising a plurality of elastomeric components have been developed.

One such arrangement is set out in US2007185453. In this embodiment, four individual elastomeric leaf components are interwoven at equal angular spacing to form the seal assembly.

This arrangement is advantageous as the overlapping structure requires less force to dilate or expand to accommodate instruments of larger diameters. Another advantage of this design is that under expansion, each individual leaf component is subject to less tension, making the seal less vulnerable to damage from surgical instruments.

A significant disadvantage of this design is that additional components, namely, the individual leaves have to be made. Furthermore, the intricacy of the assembly process adds cost and complexity to the manufacturing process.

Statements of the Invention

According to the present invention, there is provided a surgical access device comprising a seal assembly comprising a plurality of part circular sealing members each attached to a common ring which is held within the device about its longitudinal axis and with the sealing members being located radially inwards of the ring in a stacked relationship, the sealing members being movable, when not within the device, from a position radially outwards of the ring to a position radially inwards of the ring Accordingly, the sealing assembly of the invention allows an otherwise complex multi-component assembly to be moulded as a single item.

Preferably, the seal assembly comprises a single sheet of flexible material which may be arranged in a single plane with the part circular sealing members in a non-overlapping relationship.

The seal assembly is such that the sealing members extend inwardly in a radial arrangement from an outer integral support ring which, when assembled with corresponding housing components, overlap one another to form a substantially planar surface that has a thickness greater than the individual seal members and has an aperture located at its centre. This facilitates an overlapping formation to be achieved from a single component rather than the intricate assembly of multiple components.

The design of the seal assembly is such that the assembly of the sealing members means that their orientation changes to one another by a predetermined angle about the axis of the cannula such that the orifice is reduced when in an assembled state.

The outermost surfaces of the sealing members become the innermost surface of the component when in their assembled state. This makes the sealing member viable for manufacture via standard injection or compression moulding techniques.

The individual sealing members may be tapered (inclined rather than perpendicular) at their straight edges. This gives an improved airtight seal during use and also reduces friction between the seal member and a surgical instrument shaft.

The individual sealing members are semi-circular in shape. This means that, when assembled, the seal assembly forms a circular footprint when viewed from above. This is preferable for the embodiment of the design into a laparoscopic port system.

The sealing members may include a plurality of orifices adjacent their curved edges to assist in the clamping of the seal in its assembled state. The upper or lower housing may include integral posts to engage in the plurality of orifices.

Preferably, the outer perimeter of the flattened semicircular seal members are clamped between upper and lower housing components to retain the flattened arrangement during use. This is to ensure that the seal component retains the desired assembled state and does not revert back to its moulded state.

The vertically protruding members may be profiled and dimensioned in such a way that allows them to engage with their mating surface. This is to facilitate a neater arrangement upon assembly.

Preferably, the seal assembly is held within the device by a connection allowing the seal assembly to float relative to the remainder of the device. More preferably, the connection is formed from a flexible elastomeric ring of serpentine configuration.

A flotation device connected to the primary sealing member allows axial movement of small diameter surgical instruments to be absorbed and thereby maintain the airtight seal between the shaft of the surgical instrument and the inner aperture of the sealing member.

The connection may be integral with the seal assembly.

Preferably, the device includes a protective member located adjacent and above (on the proximal side) the primary sealing member, the protective member contacting, in use, said sealing members. The protective member allows the inwardly distal ends of the protective member to contact the innermost diameter of the sealing assembly during use. This is to protect the sealing assembly from potential damage caused by traumatic surgical instruments.

Preferably, the protective member comprises two components, one being located above and rotationally offset from the other. Each component may be in the form of a ring provided with two or more inwardly extending flexible leaves or flaps which allow an instrument to pass through the ring. Preferably, each component is provided with two diametrically opposed flaps.

Preferably, the device is provided with a sealing arrangement axially and distally spaced from said sealing assembly. This sealing arrangement may be a one-way valve such as a duck bill valve. This sealing arrangement provides an airtight seal when no surgical instrument is present.

The present invention further provides a seal core for a surgical access device of the invention, the seal core comprising at least the seal assembly and the protective member as described above.

The present invention also provides a method of assembling a surgical access device having a seal assembly comprising a plurality of part circumferential sealing members each connected to a common support ring, the support ring being held within the device about its longitudinal axis, the sealing members being movable, when not within the device, from a position radially outwards of the ring to a position radially inwards of the ring, the method comprising the step of moving the sealing members from a position radially outwards of the ring to a position radially inwards of the ring, so that said sealing members are in a stacked relationship.

BRIEF DESCRIPTION OF THE DRAWINGS

The accompanying drawings are as follows:

FIG. 10A shows the protection or armour layer of the device of FIG. 1 with its leaves in the open position;

FIG. 10B shows the protection or armour layer of the device of FIG. 1 with its leaves in the closed position;

FIG. 11 is a sectional view of one of the leaves of the protection layer of FIG. 10A;

FIG. 12 is a part sectional view showing the insertion of a 12 mm surgical instrument through the protection layer and seal member of the device of FIG. 1;

DETAILED DESCRIPTION OF THE INVENTION

The present invention will now be described, by way of example only, with reference to the accompanying drawings.

Figure 1:
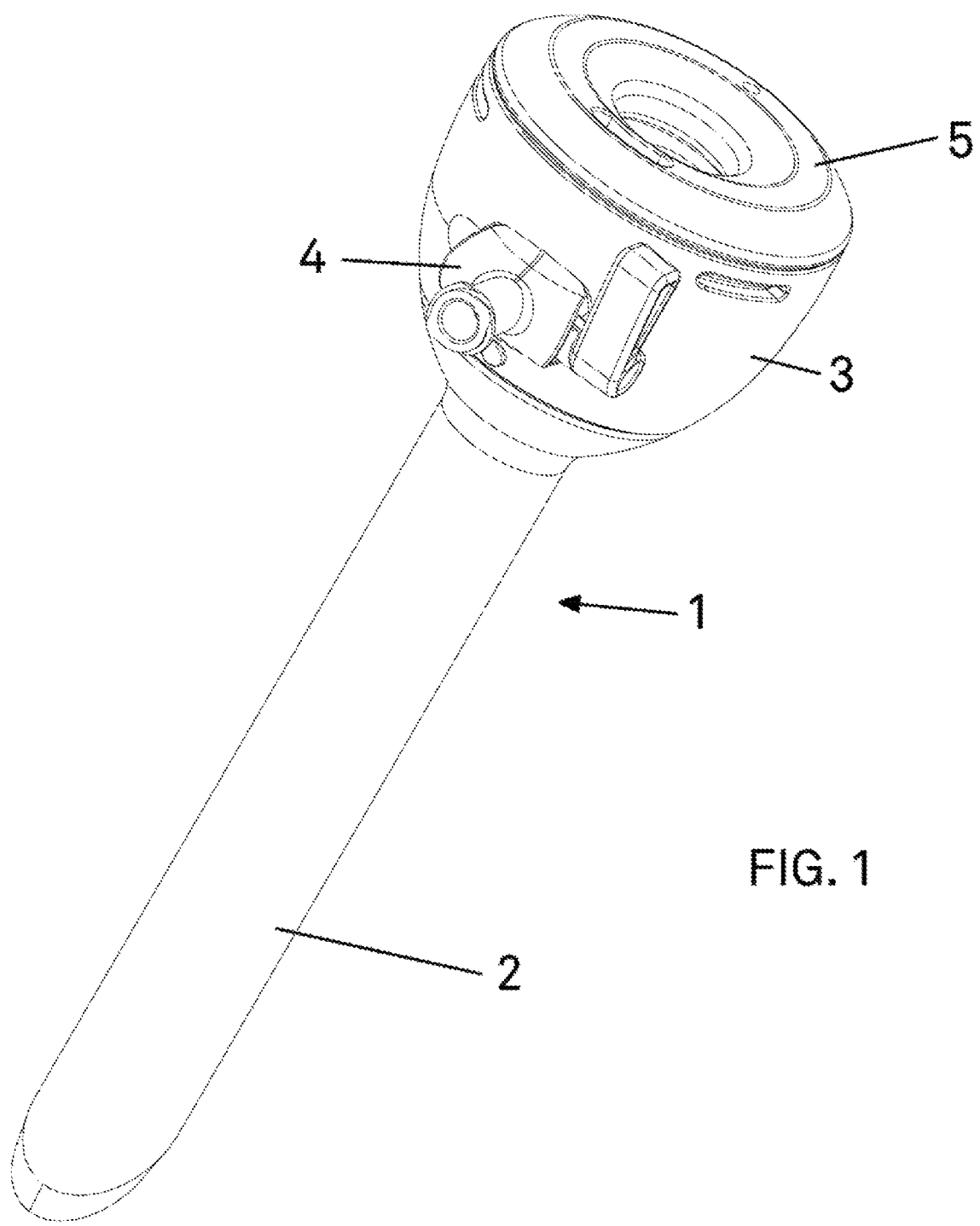
FIG. 1 is a perspective view of the full port assembly of a surgical access device of the invention.

FIG. 1 shows a port assembly 1 consisting of an elongated tube 2 for inserting the port into the abdomen, a cannula body 3, a gas tap 4 and a single use seal assembly 5. The cannula body 3 and seal assembly 5 are commonly connected to one another permanently or detachably thereby aiding production of the parts and also giving the potential for the same cannula to be used with multiple seal assemblies.

Figure 2:
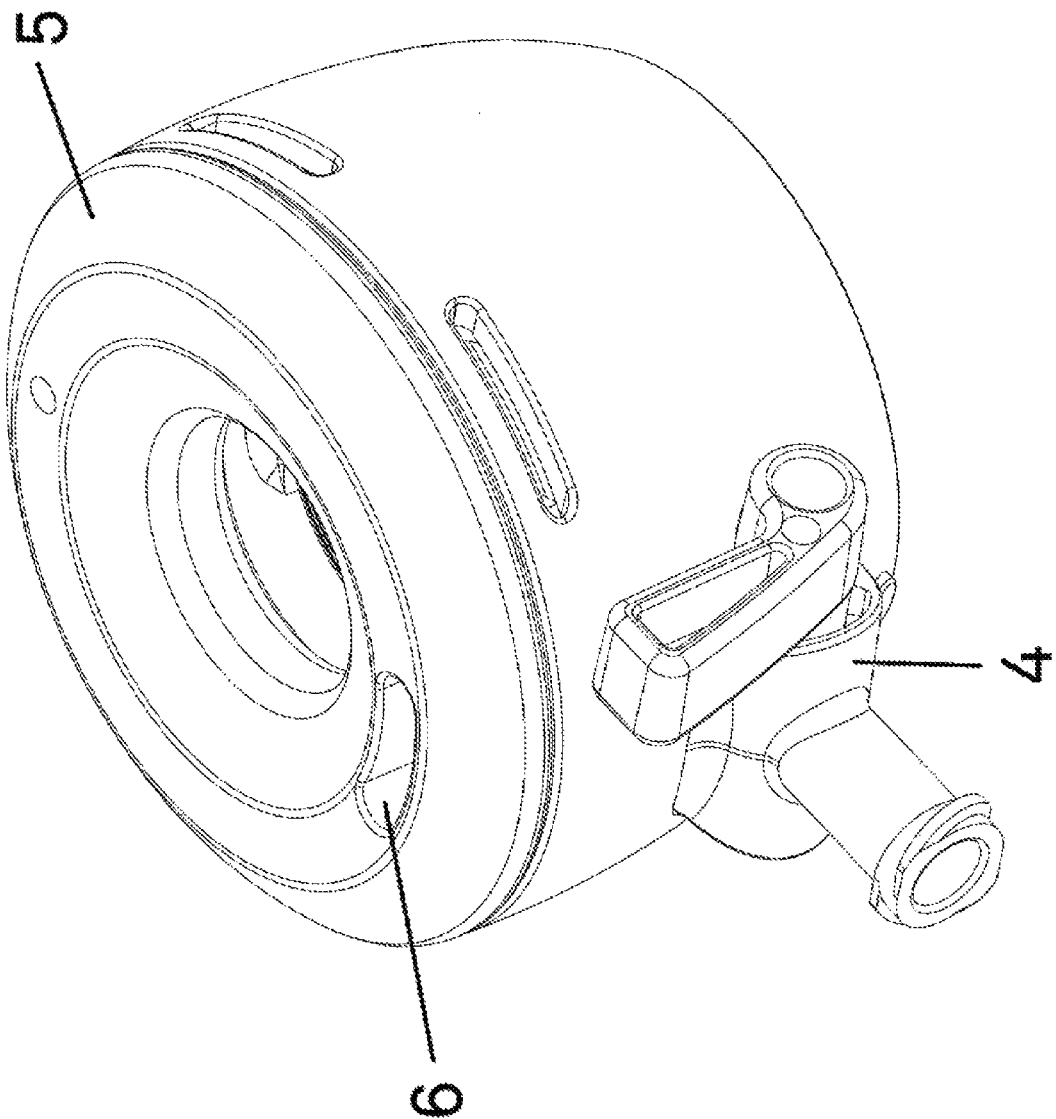
FIG. 2 is a perspective view of the seal housing of the device of FIG. 1.

FIG. 2 shows the seal unit detached from the tube 2. At its upper surface the unit is provided with a slot or recess 6 which enables an instrument such as an optical trocar provided with a corresponding protrusion to engage with the seal unit to maintain a desired rotational alignment between the instrument and the seal unit.

Figure 3:
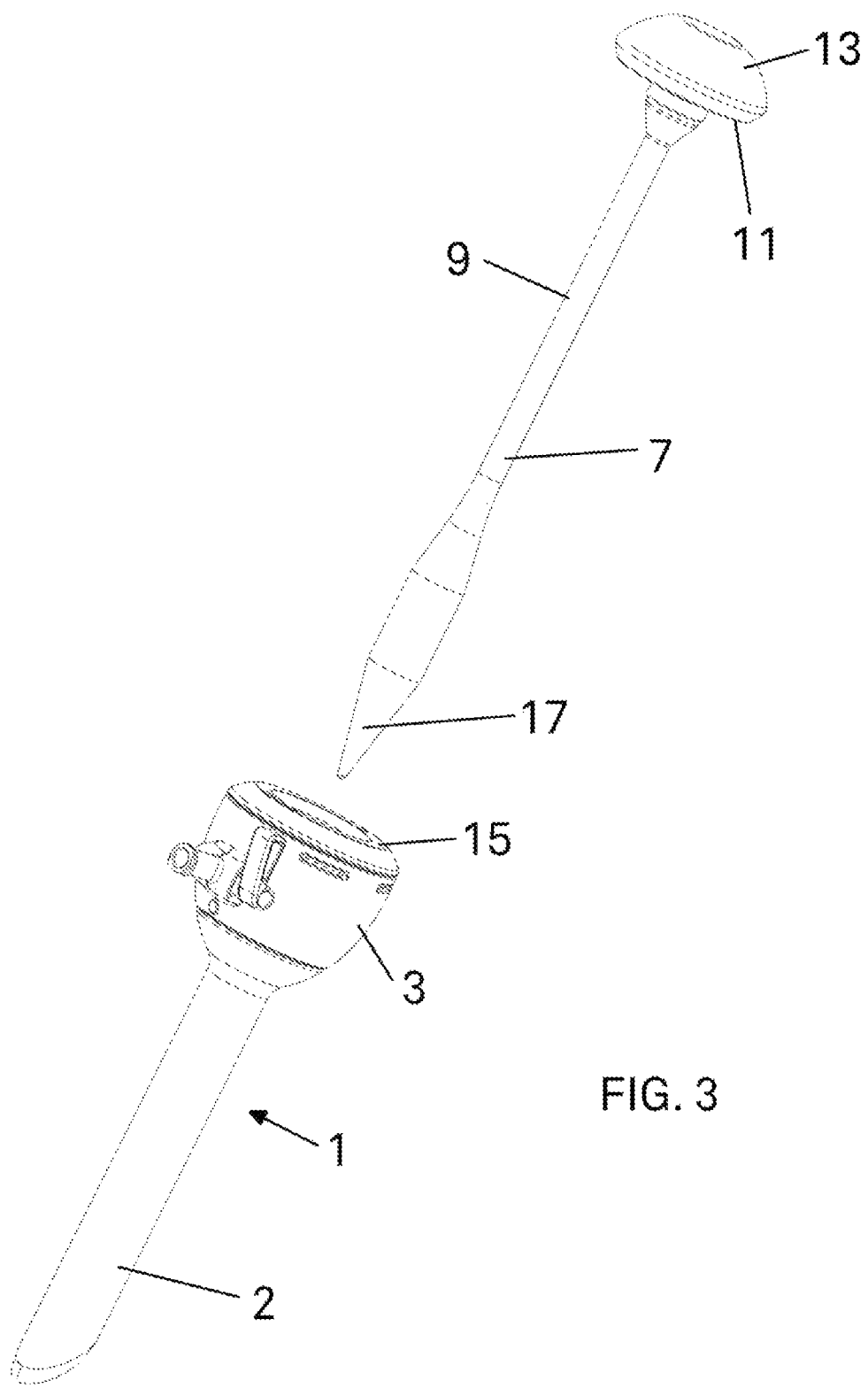
FIG. 3 is a perspective view of the device of FIG. 1 in conjunction with a trocar assembly prior to instrument insertion therethrough.

FIG. 3 illustrates the port assembly 1 in conjunction with a trocar 7 which, in use, is pushed though the cannula and seal assembly 1. When inserted, shaft 9 of trocar 7 extends down through elongate tube 2 until the underside 11 of trocar 13 mates against the upper surface 15 of cannula body 3. At this point the trocar tip 17 extends out of elongate tube 2 by a predetermined amount.

Figure 4:
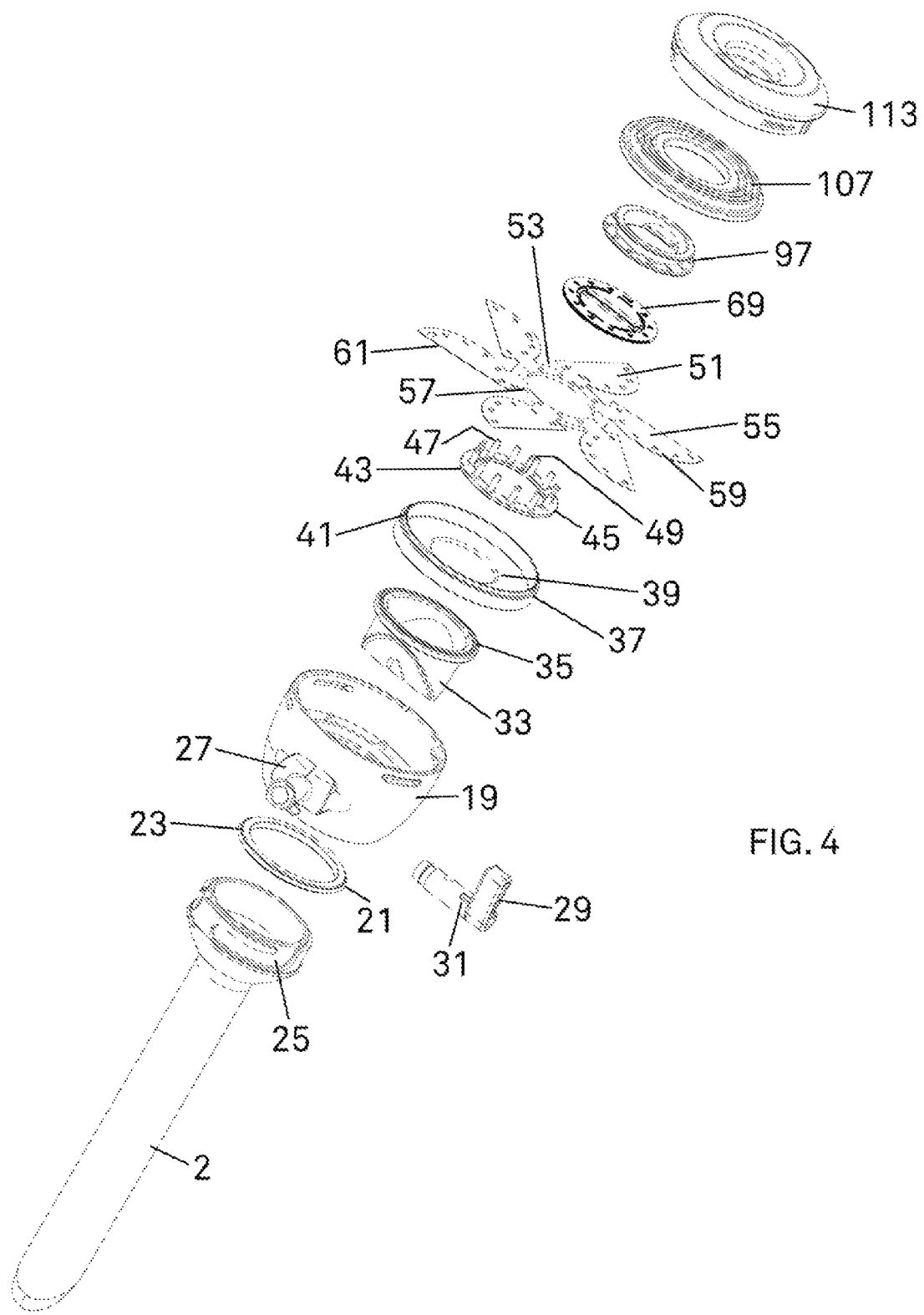
FIG. 4 is an exploded perspective view of the device of FIG. 1 showing the constituent parts of the device.

Referring to FIG. 4, seal assembly 1 includes the elongate (or cannula sheath) tube 2 to which the seal housing 19 is attached via face seal or gasket 21. Gasket 21 is provided with a circumferentially and outwardly extending lip 23 which engages with a corresponding recess in the inner wall of seal housing 19.

The attachment between cannula sheath tube 2 and seal housing 19 is of the bayonet type, inner circumferentially spaced projections (not shown) on the seal housing 19 engaging in slots 25 of cannula sheath tube 2. The seal housing 19 can be first pushed down on the cannula sheath tube 2 with the projections moving along axially extending portions of the slots 25.

Gas tap 4 includes a tap body 27, which is integral with the seal housing 19, and a lever 29 which carries an integral stop member 31. Stop member 31 engages with features located within tap body 27 to limit the range of movement of lever 29. This assists the surgeon by indicating when the tap is in its fully open or fully closed condition.

Duck bill valve 33, having an upper circumferential lip 35, seats on a corresponding circumferential ledge located within seal housing 19.

An intermediate plate 37 locates within seal housing 19 above valve 33. It provides a support surface 39 for the seal and also provides a lip 41 on which the bellows member (to be mentioned below) is mounted.

Located on intermediate plate 37 is lower clamp 43 which is in the form of a flat ring 45 having extending axially from one surface a series of integral pegs 47 which are equally spaced apart. These pegs 47 are all of similar shape and size, being circular in cross section, apart from one peg 49 which is key shaped in cross section.

Instrument seal member 51 is made from a thin flexible plastics material and includes central, flat ring 53 to which six part-circular petals 55 are integrally connected. As shown in FIG. 4, the seal member 51 is a planar member although, as will be described below, the petals can be folded over for use within the seal unit.

Ring 53 has located therein equally spaced apart holes 57, all of which are circular apart from one which is keyhole shaped. Ring 53 is for location on lower clamp 43 with pegs 47 of lower clamp 43 extending through corresponding holes 57 of ring 53.

Each petal 55 has a part circular edge 59 and a straight edge 61. The petals 55 are equally spaced apart about ring 53 to which each petal 55 is connected by a living hinge which is indicated at 63 located at the part circular edge of the petal close to one end of the straight edge. Each petal 55 is provided with a plurality of holes 65 which are equally spaced apart and extend circumferentially and spaced inwardly from the part circular edge of the petal. Most of the holes 65 are circular. However, three of the petals 55 have keyhole shaped holes 67 and they are located at different positions in their respective petals for a reason that will be made clear below.

Located above seal member 51 is a protection or armour layer 69 which is made of flexible plastics material. As best seen in FIGS. 10A and 10B, armour layer 69 comprises two substantially circular elements 71 and 73 interconnected at their peripheral edges by an integral living hinge 75. Both elements 71 and 73 are formed of resilient plastics which is more robust than that of seal member 51. When located within the seal housing 19, element 71 lies below element 73.

The protective or armour layer 69 may, instead of being a single piece, alternatively be formed of two separate elements corresponding to elements 71 and 73 shown in FIG. 10A.

Circular element 71 comprises an outer ring area 77 in which are located a series of equally spaced apart holes 79, which are circular except for one keyhole shaped hole 81 and which are for location over the pegs 47 of lower clamp 43. Within ring area 77 are located two flaps 83 each of which is broadly semicircular in shape with a gently curved edge 85 extending between the rounded ends of a peripheral edge 87 which extends slightly inwardly and parallel to ring area 77. The gently curved edges of the two flaps 83 face each other on either side of a line passing through the centre of circular element 71, the space between the opposite edges 85 decreasing from a relatively wide spacing at the centre of element 71 to narrower spacings at the radially outer positions. Each flap 83 is connected at its peripheral edge 87 to the ring area 77 by two spaced apart integral links 89. This arrangement is such that the flaps 83 can be resiliently flexed out of the plane of the ring area 77.

Circular element 73 is of similar configuration to that of element 71 but with its two flaps 91 being aligned at 90° to the flaps 83 of element 71. Each flap 91 has, adjacent its gently curved edge a strip 93 which has steeply reducing thickness from the body of the flap towards its free edge. The flaps 83 of element 71 have similar edge portions which do not appear in FIG. 10A but can be seen at 95 in FIG. 10B when the two circular elements 71, 73 are superimposed. These edge portions 93, 95 allow the edges of the flaps to be compliant to accommodate variations in the profile of the shaft of a surgical instrument especially when the instrument is being retracted.

FIG. 12 illustrates the positions of both petals 51 and flaps 83 and 91 (shown as one item in FIG. 12) during retraction of an instrument 96 from the seal assembly.

Figure 5A:
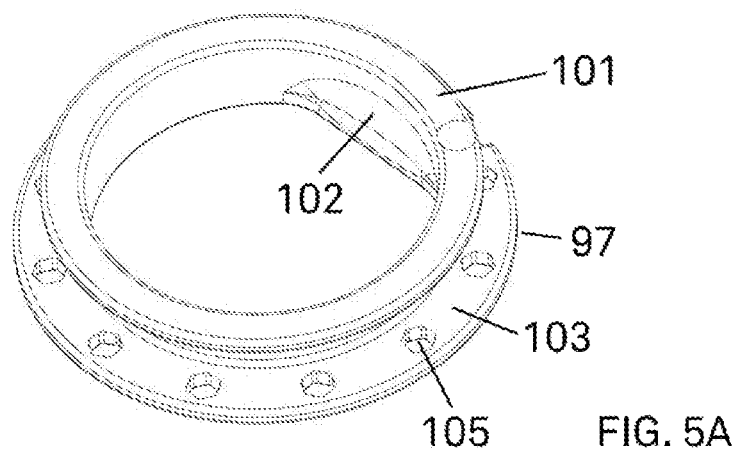
FIG. 5A is a perspective view of the upper clamp of the device of FIG. 1.
Figure 5B:
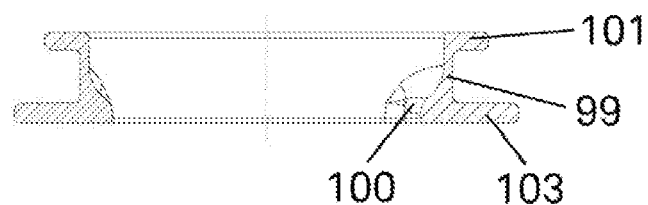
FIG. 5B is a sectional view of the upper clamp of FIG. 5A.

Located above armour layer 69 is upper clamp 97 which functions to hinder the inversion of armour layer 69. As best seen in FIGS. 5A and 5B, upper clamp 97 is a ring having an axial wall 99 extending between an upper, outwardly extending flange 101 and a relatively wider lower, outwardly extending flange 103. Flange 103 is provided with equally spaced apart hexagonal holes 105 to enable the upper clamp to be located on the pegs 47.

Extending inwardly from axial wall 99 of clamp 97 are two diametrically opposed flats or ledges 100 which assist in preventing the armour layer inverting on withdrawal of an instrument from the seal assembly. Each ledge 100 has a radial lower surface and a gently and smoothly inclined upper surface 102, the latter facilitating the smooth entry of an instrument into the seal assembly.

Figure 6:
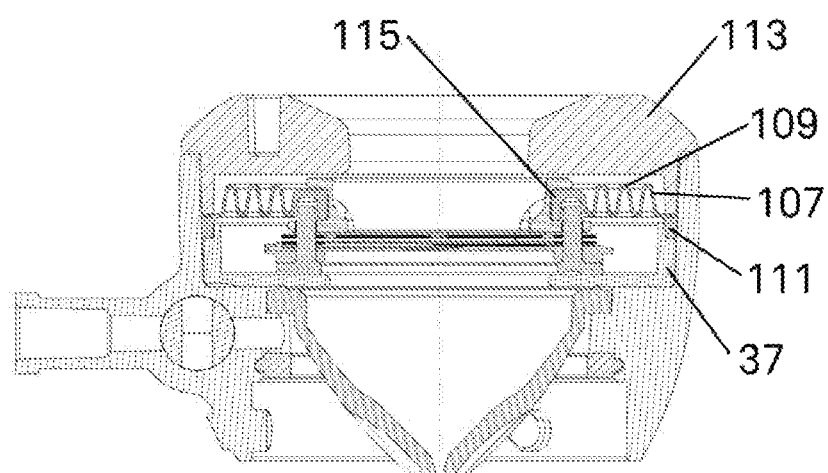
FIG. 6 is a sectional view of the seal assembly of the device of FIG. 1.
Figure 7:
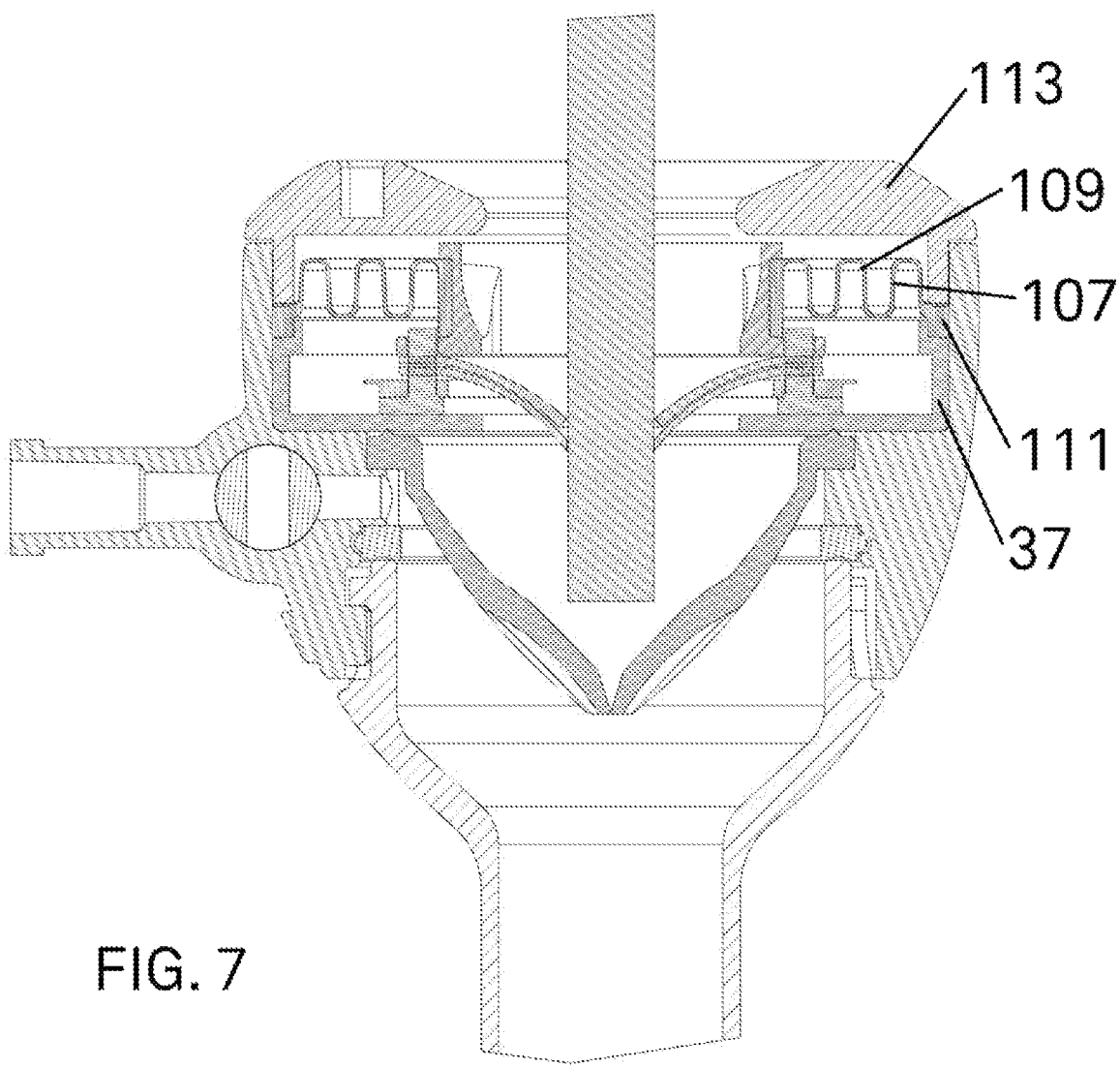
FIG. 7 is a sectional view of the seal assembly of the device of FIG. 1 and in conjunction with a 5 mm surgical instrument.
Figure 8:
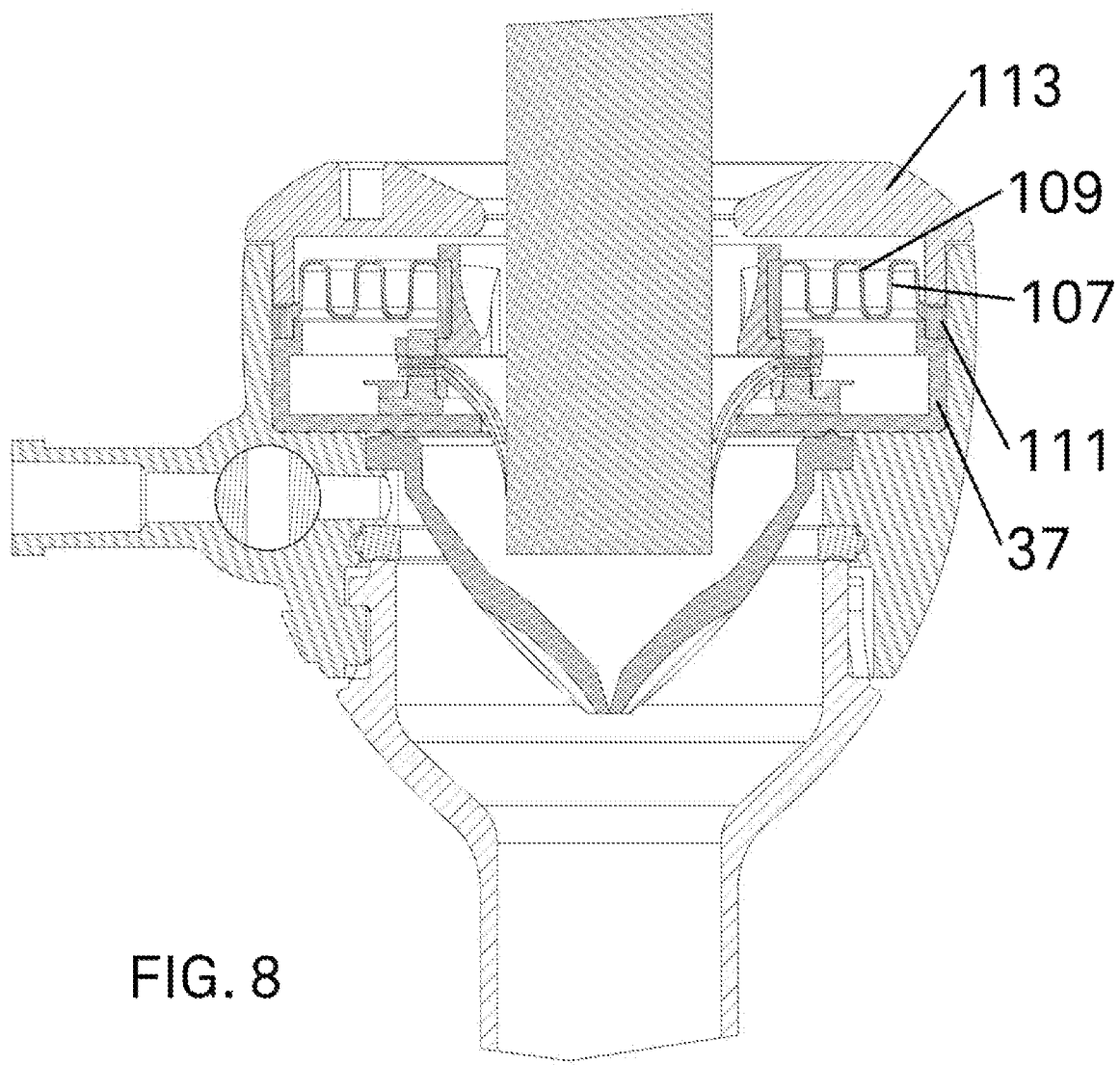
FIG. 8 is a sectional view of the seal assembly of the device of FIG. 1 and in conjunction with a 12 mm surgical instrument.

A flotation or bellows element 107 is located alongside upper clamp 97. As best seen in FIGS. 6, 7 and 8, flotation element 107 is a ring of flexible elastomeric material which has a central portion 109 of serpentine configuration. The outer edge of the central portion 109 is provided with an enlarged head portion 111 which enables the flotation element 107 to be trapped between intermediate plate 37 and seal housing cap 113. The inner edge of the central portion 109 is provided with a thickened tail portion 115 which enables the flotation element to be fitted at this edge between the flanges 101 and 103 of upper clamp 97. Flotation element 107 allows an instrument inserted into to the seal assembly to have a considerable degree of orbital movement (radial float) without loss of the gas pressure during an operation.

The cannula 3 is assembled for use in the following manner. The stopcock lever 29 is inserted in the stopcock body 29. The gasket 21 is inserted. The valve 33 is introduced into the housing 19. The intermediate plate is then positioned on top of the valve.

Figure 9A:
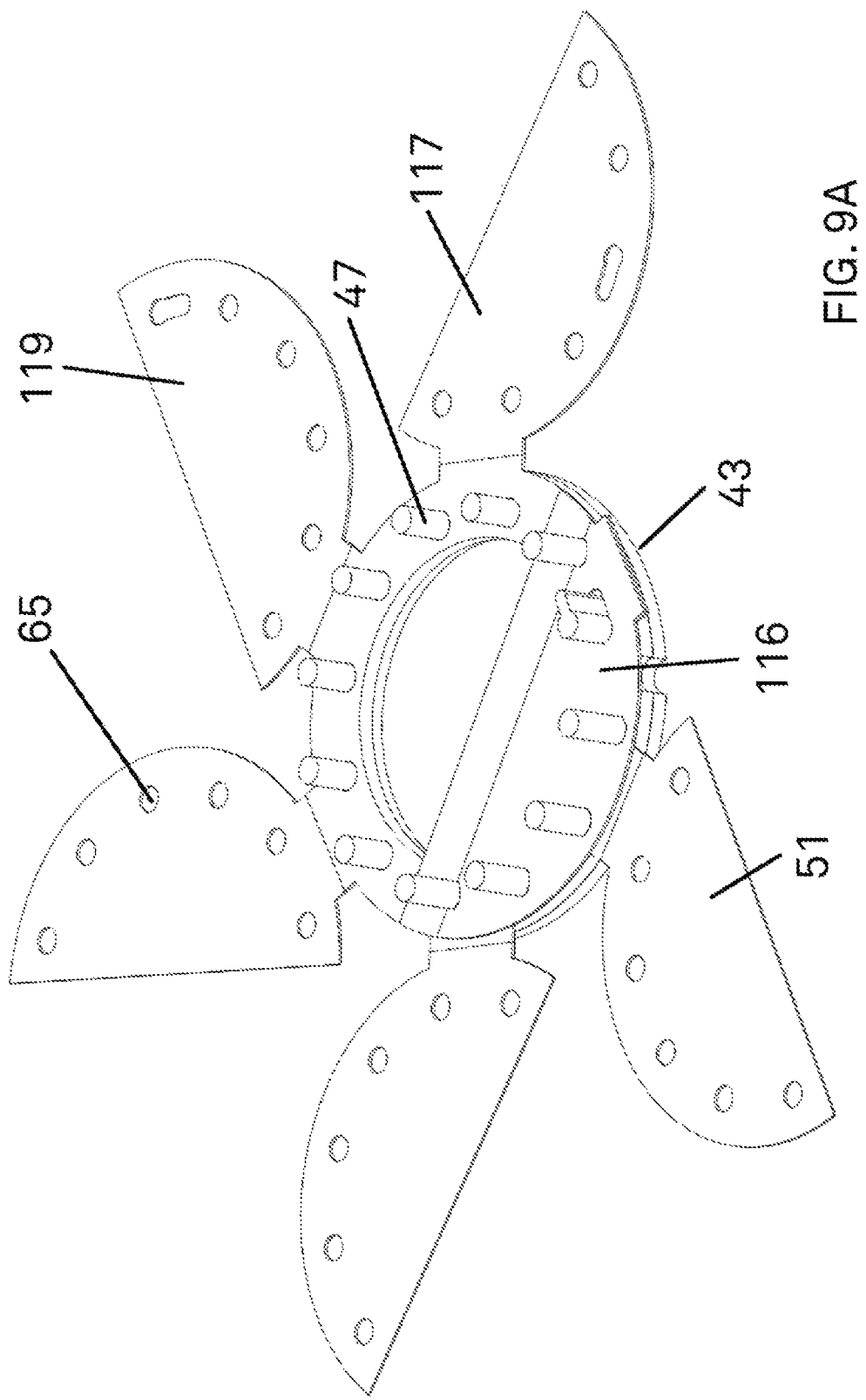
FIG. 9A to 9E show successive stages in the folding of the petals of the device of FIG. 1 into their closed positions.
Figure 9B:
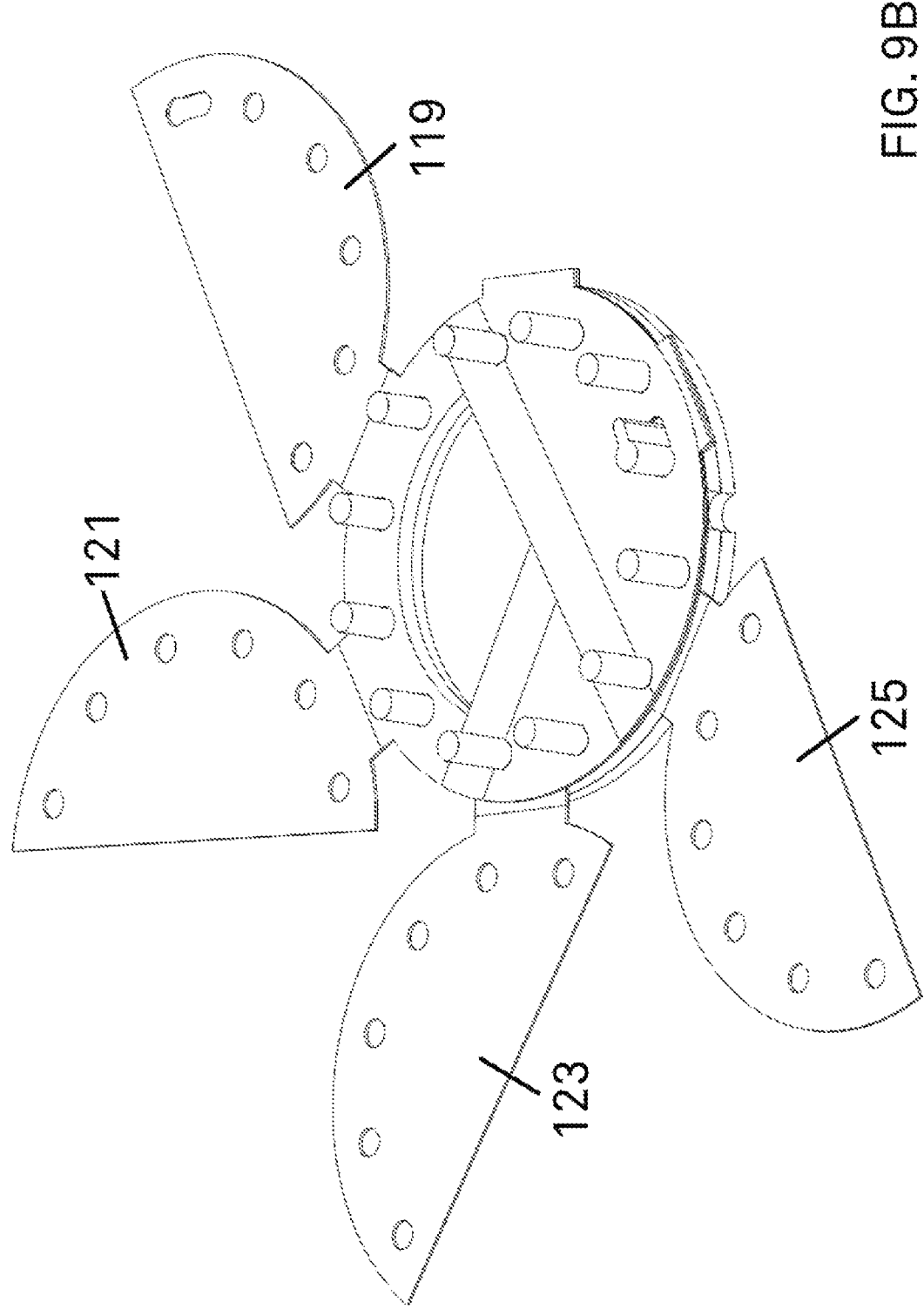
Figure 9C:
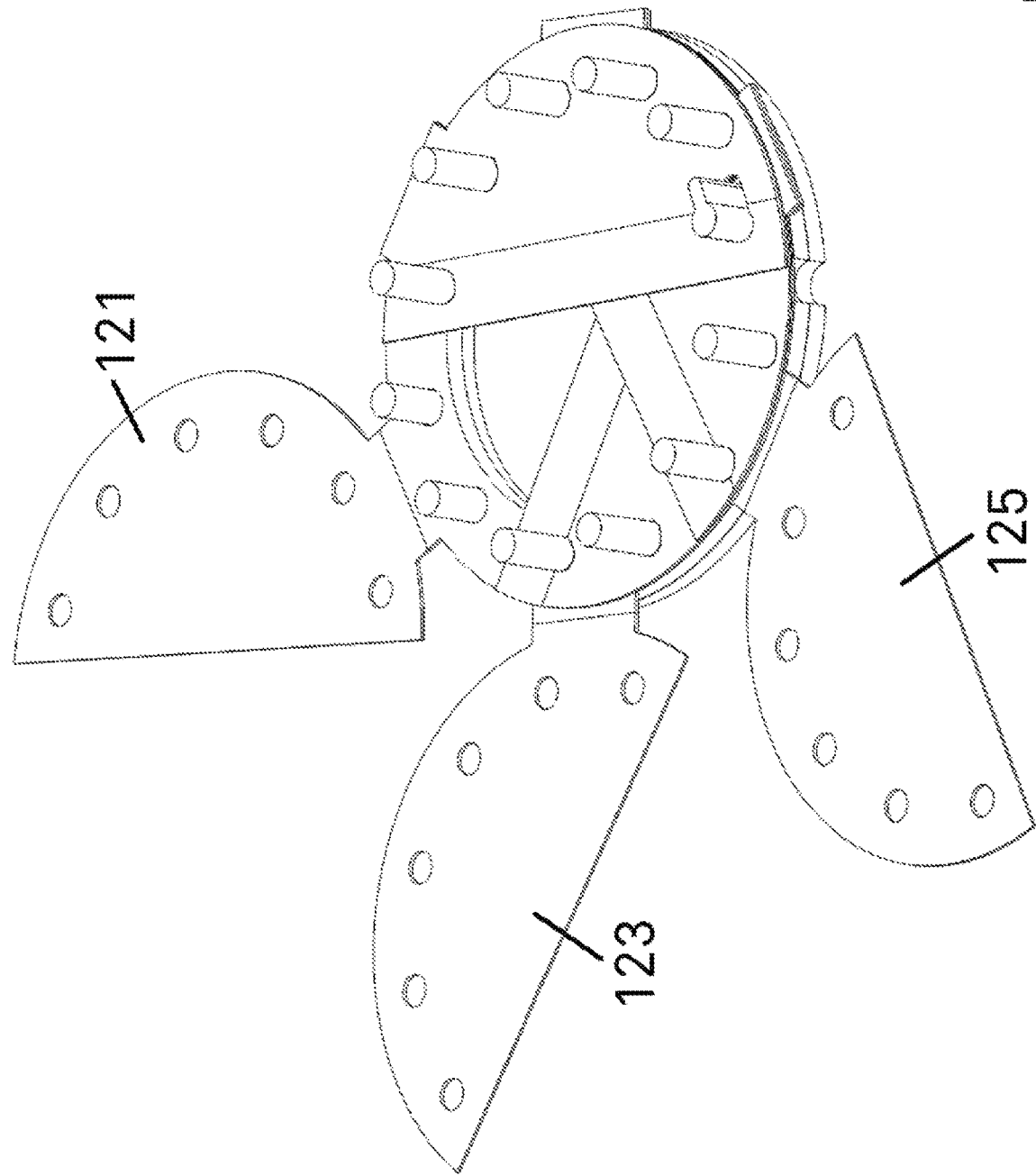
Figure 9D:
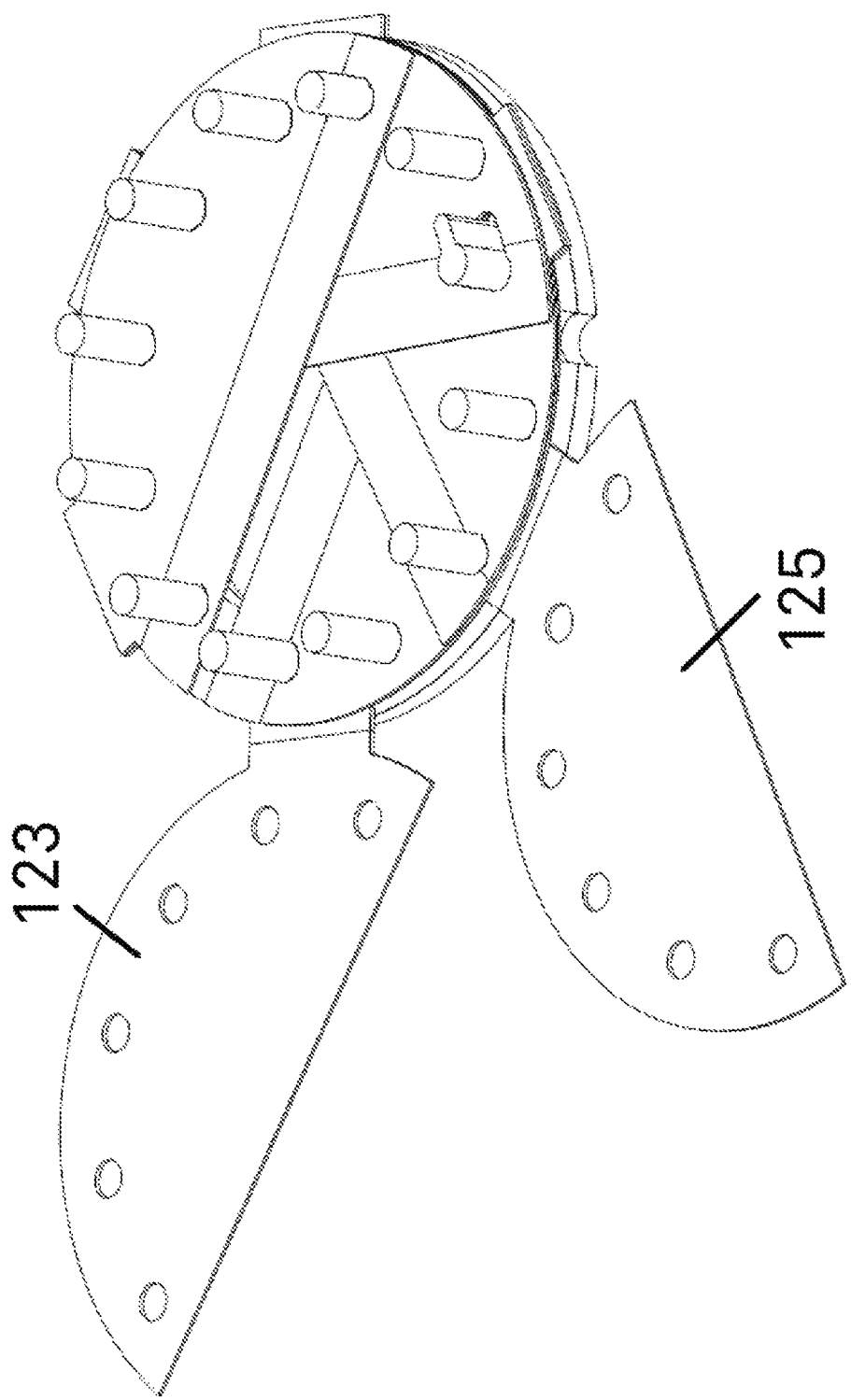
Figure 9E:
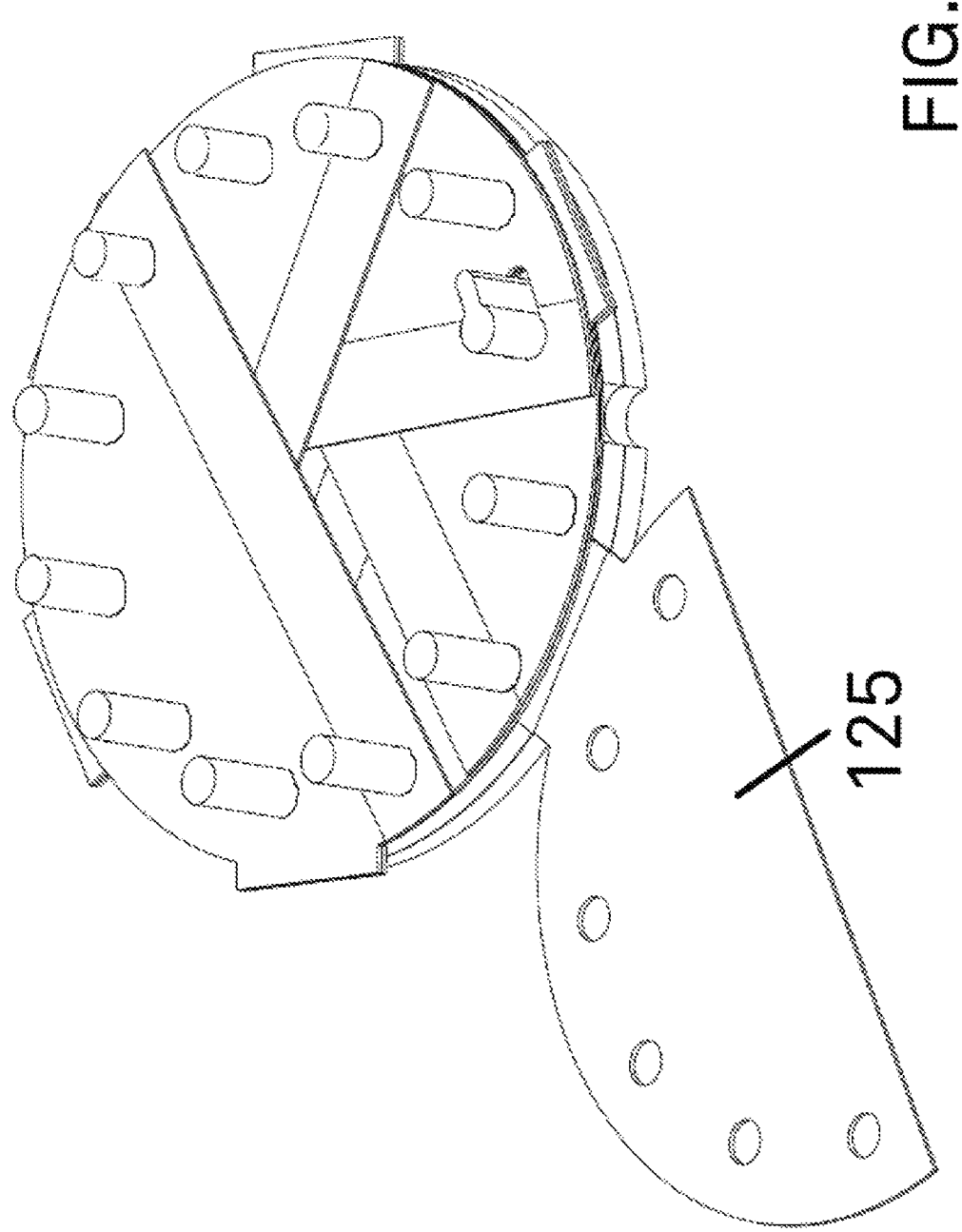

Next the instrument seal member 51 is folded onto the lower clamp 43. This process is illustrated in FIGS. 9A to 9E. FIG. 9A shows the position after one petal 116 has been folded over so that the holes 65 locate on certain of the pegs 47. Then, previously adjacent petal 117 is folded over to reach the position illustrated in FIG. 9B and this is followed by the successive folding over of petals 119, 121 and 123, as illustrated in FIGS. 9C to 9E. Finally, petal 125 is folded over so that all petals are located on the pegs 47. This is achieved by folding each petal, after the first petal, over the previously folded over petals and not by interleaving any petal with previously folded over petals. The result is a simple stacking of petals and this procedure avoids the need for a relatively difficult process of manoeuvring one or more petals to produce a woven configuration.

Each petal is in effect moved radially with respect to the lower clamp and this requires that three of the petals 115, 117 and 119 each have a keyhole shaped hole which is located in a different position on the three petals so that the radial movement causes the keyhole shaped holes all to locate on key shaped peg 49 of lower clamp 43.

Figure 13:
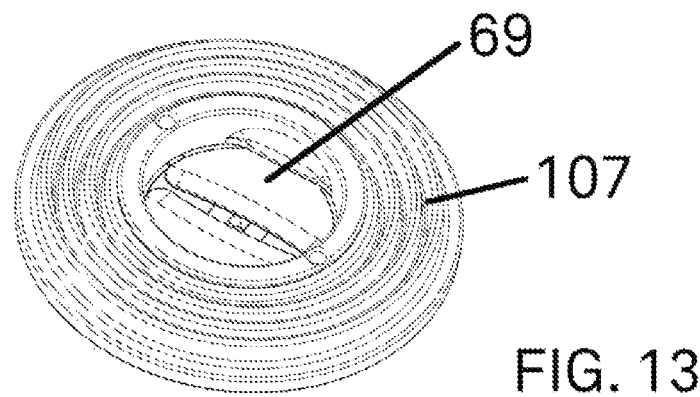
FIG. 13 is a perspective view of the seal core of the assembly of FIG. 1.
Figure 14:
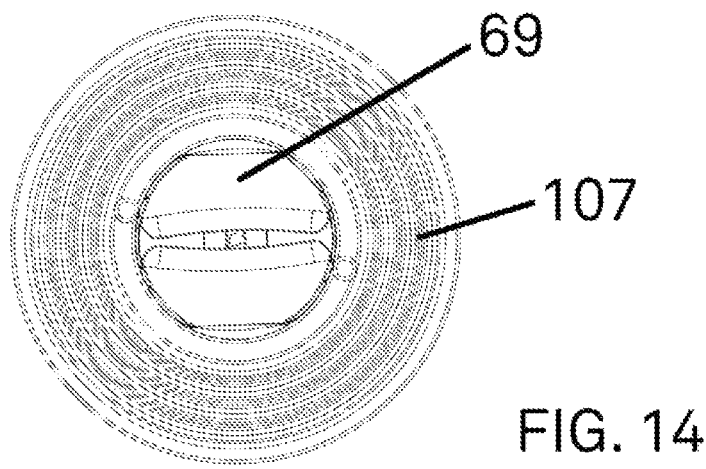
FIG. 14 is a top plan view of the seal core of FIG. 13.

Referring to FIGS. 4, 13 and 14 of the accompanying drawings, items 43, 51, 69, 97 and 107 together comprise a unit which is the seal core for the overall assembly. This unit may be used in other configurations of surgical access devices.

The invention claimed is:

1. A surgical access device comprising a seal assembly comprising a plurality of part circular sealing members each attached to a common ring which is held within the device about its longitudinal axis and with the part circular sealing members being located radially inwards of the common ring in a stacked relationship, characterised in that the seal assembly comprises a single sheet of flexible material which is configured to be arranged in a single plane with the part circular sealing members in a non-overlapping relationship and in that the part circular sealing members are foldable, when not within the device, from a position radially outwards of the common ring to a position radially inwards of the common ring.

2. A device according to claim 1, wherein the seal assembly is held within the device by a connection allowing the seal assembly to float relative to the remainder of the device.

3. A device according to claim 2, wherein the connection is formed from a flexible elastomeric ring of serpentine configuration.

4. A device according to claim 2, wherein the connection is integral with the seal assembly.

5. A device according to claim 1, wherein the stacked part circular sealing members together have a thickness greater than that of the individual part circular sealing members and define a central aperture.

6. A device according to claim 1, wherein the part circular sealing members are substantially semi-circular.

7. A device according to claim 1, wherein the part circular sealing members include a plurality of orifices adjacent their edges.

8. A device according to claim 1, wherein the device includes a protective member located on a proximal side of the seal assembly, the protective member contacting, in use, said part circular sealing members.

9. A device according to claim 8, wherein the protective member comprises two elements, one of said elements being located above and rotationally offset from the other of said elements.

10. A device according to claim 9, wherein each element comprises a ring with flaps inwardly extending therefrom.

11. A device according to claim 1, wherein the device is provided with a sealing arrangement axially spaced from said sealing assembly.

12. A device according to claim 11, wherein the sealing arrangement is a duck bill valve.

13. A seal core comprising a seal assembly and a protective member, the seal core being for use in a surgical access device, and the seal assembly comprising a plurality of part circular sealing members each attached to a common ring which is held within the device about its longitudinal axis and with the part circular sealing members being located radially inwards of the common ring in a stacked relationship, wherein the seal assembly comprises a single sheet of flexible material which is configured to be arranged in a single plane with the part circular sealing members in a non-overlapping relationship and in that the part circular sealing members are foldable, when not within the device, from a position radially outwards of the common ring to a position radially inwards of the common ring.

14. A method of assembling a surgical access device having a seal assembly comprising a plurality of part circular sealing members each connected to a common support ring, the common support ring being held within the device about its longitudinal axis, the method comprising the step of moving the part circular sealing members from a position radially outwards of the ring to a position radially inwards of the common support ring, so that said part circular sealing members are in a stacked relationship, wherein the seal assembly comprises a single sheet of flexible material which is configured to be arranged in a single plane with the part circular sealing members in a non-overlapping relationship and in that the part circular sealing members are foldable, when not within the device, from a position radially outwards of the common support ring to a position radially inwards of the common support ring.

* * * * *